US009822073B2

(12) United States Patent
Boaz et al.

(10) Patent No.: US 9,822,073 B2
(45) Date of Patent: Nov. 21, 2017

(54) HETEROCYCLIC AMPHOTERIC COMPOUNDS

(71) Applicant: Eastman Chemical Company, Kingsport, TN (US)

(72) Inventors: Neil Warren Boaz, Kingsport, TN (US); Matthew Allen Boone, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 15/283,739

(22) Filed: Oct. 3, 2016

(65) Prior Publication Data

US 2017/0022159 A1 Jan. 26, 2017

Related U.S. Application Data

(62) Division of application No. 14/518,517, filed on Oct. 20, 2014, now Pat. No. 9,533,951.

(51) Int. Cl.

| | | |
|---|---|---|
| *C07D 211/34* | (2006.01) | |
| *A61K 8/49* | (2006.01) | |
| *C07D 213/55* | (2006.01) | |
| *C07D 213/56* | (2006.01) | |
| *A61Q 19/00* | (2006.01) | |
| *C12P 17/12* | (2006.01) | |
| *B01F 17/00* | (2006.01) | |
| *C07D 211/22* | (2006.01) | |
| *C07D 211/44* | (2006.01) | |
| *C07D 211/58* | (2006.01) | |
| *C07D 213/30* | (2006.01) | |
| *C07D 213/40* | (2006.01) | |
| *A61Q 5/00* | (2006.01) | |
| *C07D 211/62* | (2006.01) | |
| *C07D 213/75* | (2006.01) | |
| *C07D 211/46* | (2006.01) | |
| *C07D 213/68* | (2006.01) | |

(52) U.S. Cl.
CPC .......... *C07D 211/34* (2013.01); *A61K 8/4926* (2013.01); *A61Q 5/00* (2013.01); *A61Q 19/00* (2013.01); *B01F 17/0042* (2013.01); *C07D 211/22* (2013.01); *C07D 211/44* (2013.01); *C07D 211/46* (2013.01); *C07D 211/58* (2013.01); *C07D 211/62* (2013.01); *C07D 213/30* (2013.01); *C07D 213/40* (2013.01); *C07D 213/55* (2013.01); *C07D 213/56* (2013.01); *C07D 213/68* (2013.01); *C07D 213/75* (2013.01); *C12P 17/12* (2013.01); *A61K 2800/10* (2013.01); *A61K 2800/30* (2013.01)

(58) Field of Classification Search
CPC ... C07D 211/40; C07D 213/20; C07D 213/30
USPC .................................. 546/225, 314
See application file for complete search history.

(56) References Cited

U.S. PATENT DOCUMENTS

| | | | |
|---|---|---|---|
| 2,781,349 A | 2/1957 | Mannheimer | |
| 3,001,997 A * | 9/1961 | Mannheimer et al. | C07D 207/20 424/76.8 |
| 3,280,178 A | 10/1966 | Barbour | |
| 3,280,179 A | 10/1966 | Ernst | |
| 3,915,882 A | 10/1975 | Nirschl et al. | |
| 4,259,191 A | 3/1981 | Wagner | |
| 4,687,602 A | 8/1987 | Ballschuh et al. | |
| 4,879,204 A | 11/1989 | Ishigaki et al. | |
| 5,696,070 A | 12/1997 | Tachizawa et al. | |
| 5,851,982 A | 12/1998 | Sakata et al. | |
| 5,876,705 A | 3/1999 | Uchiyama et al. | |
| 5,972,877 A | 10/1999 | Tsuda et al. | |
| 6,365,560 B1 | 4/2002 | Chopra et al. | |
| 7,667,067 B1 | 2/2010 | Clendennen et al. | |
| 7,923,428 B2 | 4/2011 | Geffroy et al. | |
| 8,889,373 B2 | 11/2014 | Clendennen | |
| 8,900,625 B2 | 12/2014 | Damaj et al. | |
| 9,120,846 B2 * | 9/2015 | Haymore ............. | B01D 15/325 205/123 |
| 9,381,147 B2 * | 7/2016 | Fevola et al. ......... | A61K 8/416 205/123 |
| 2004/0101505 A1 | 5/2004 | Payne et al. | |
| 2006/0035807 A1 | 2/2006 | Kasturi et al. | |
| 2007/0042030 A1 | 2/2007 | Cevc | |
| 2010/0016198 A1 | 1/2010 | Bernhardt et al. | |

(Continued)

FOREIGN PATENT DOCUMENTS

| | | |
|---|---|---|
| CN | 103 468 228 A | 12/2013 |
| DE | 1 240 872 B | 5/1967 |

(Continued)

OTHER PUBLICATIONS

W.M. Wu et al., "Stereoisomers of N-substituted soft anticholinergics and their zwitterionic metabolite based on glycopyrrolate—syntheses and pharmacological evaluations," Pharmazie, vol. 63, pp. 200-209 (2008).
Copending U.S. Appl. No. 14/856,656, filed Sep. 17, 2015.
Copending U.S. Appl. No. 14/856,830, filed Sep. 17, 2015.
Int'l Search Report issued in Int'l Application No. PCT/US2015/053426.
Int'l Search Report issued in Int'l Application No. PCT/US2015/055263.
Int'l Search Report and Written Opinion issued in Int'l Appl. No. PCT/US2016/049972 dated Nov. 16, 2016.
Int'l Search Report and Written Opinion issued in Int'l Appl. No. PCT/US2016/050470 dated Nov. 15, 2016.
C. Tastet et al., "Structure-efficiency relationships of zwitterionic detergents as protein solubilizers in two-dimensional electrophoresis," Proteomics 2003, 3, 111-121.
English machine translation of DE 1 240 872 B, pp. 1-8 (May 24, 1967).
English machine translation of EP 205 626, pp. 1-5 (Dec. 30, 1986).
English machine translation of JP 06-184934, pp. 1-12 (Jul. 5, 1994).

(Continued)

*Primary Examiner* — Taofiq A Solola
(74) *Attorney, Agent, or Firm* — Phan Law Group PLLC

(57) ABSTRACT

Disclosed are a variety of amphoteric compounds having a heterocyclic quaternary nitrogen group. The heterocycle includes pyridines, piperidines, and pyrrolidines, and is linked to the hydrophobe via either an amide or an ester linkage. These heterocyclic amphoteric compounds can be advantageously prepared in high yield and purity by a two-step chemoenzymatic process, and have excellent surfactant properties.

28 Claims, No Drawings

(56) References Cited

U.S. PATENT DOCUMENTS

| | | | |
|---|---|---|---|
| 2010/0159393 | A1 | 6/2010 | Fiebag et al. |
| 2011/0300093 | A1 | 12/2011 | Bendejacq et al. |
| 2012/0040395 | A1 | 2/2012 | Clendennen |
| 2012/0277324 | A1 | 11/2012 | Burk et al. |
| 2014/0345483 | A1 | 11/2014 | Imaizumi et al. |
| 2016/0271034 | A1 | 9/2016 | Fevola et al. |

FOREIGN PATENT DOCUMENTS

| | | |
|---|---|---|
| DE | 2 252 687 A1 | 5/1974 |
| DE | 274 332 A3 | 12/1989 |
| DE | 278 053 A1 | 4/1990 |
| DE | 278 054 A1 | 4/1990 |
| DE | 278 061 A1 | 4/1990 |
| EP | 0 205 626 A1 | 12/1986 |
| EP | 0205626 A1 | 12/1986 |
| EP | 2 818 930 A1 | 12/2014 |
| JP | S42 16415 B1 | 9/1967 |
| JP | S42 26523 B1 | 12/1967 |
| JP | S56 141375 A | 11/1981 |
| JP | 6-184934 A | 7/1994 |
| JP | 06184934 A | 7/1994 |
| JP | 7-309724 A | 11/1995 |
| JP | 10-97065 | 4/1998 |
| WO | 1998/033879 A1 | 8/1998 |
| WO | 2007/023336 A2 | 3/2007 |
| WO | 2007/059021 A1 | 5/2007 |
| WO | 2009/136396 A2 | 11/2009 |
| WO | 2011/114876 A1 | 9/2011 |
| WO | 2011/146595 A2 | 11/2011 |
| WO | 2012/024233 A2 | 2/2012 |
| WO | 2012/061098 A1 | 5/2012 |
| WO | 2012/080018 A2 | 6/2012 |
| WO | 2013/052087 A1 | 4/2013 |
| WO | 2016/064549 A1 | 4/2016 |

OTHER PUBLICATIONS

English machine translation of JP0730724, pp. 1-26 (Unknown).
Copending U.S. Appl. No. 15/170,097, filed Jun. 1, 2016.
Parris et al., "Soap Based Detergent Formulation: XXIV. Sulfobetaine Derivatives of Fatty Amides," J. Am. Oil Chem. Soc., vol. 54, pp. 294-296 (1977).
ASTM D 1173-07, Standard Test Method for Foaming Properties of Surface-Active Agents, pp. 1-3 (2007).
Chattopadhyay et al., "Fluorimetric Determination of Critical Micelle Concentration Avoiding Interference from Detergent Charge," Analytical Biochem., vol. 139, pp. 408-412 (1984).
Boaz et al., Copending U.S. Appl. No. 14/518,505, filed Oct. 20, 2014.
Boaz et al., Copending U.S. Appl. No. 14/518,517, filed Oct. 20, 2014.
"Supplementary Examination Guidelines for Determining Compliance with 35 U.S.C. 112 and for Treatment of Related Issues in Patent Applications," Fed. Reg., vol. 76, No. 27, pp. 7162-7175 and slides 1, 64-67 (2011).
Human English Translation of CN 103 468 228, pp. 1-9 (2013).
T.A. Spencer et al, "Zwitterionic Sulfobetaine Inhibitors of Squalene Synthase," J. Org. Chem., vol. 64, pp. 807-818 (1999).
C.Y. Guo et al., "Synthesis of Surface-Functionalized, Probe-Containing, Polymerized Vesicles Derived from Ammonium Bromide Surfactants," Langmuir, vol. 8, pp. 815-823 (1992).
S. Hashmi et al., "Supramolecular Interaction Controlled Diffusion Mechanism and Improved Mechanical Behavior of Hybrid Hydrogel Systems of Zwitterions and CNT," Macromolecules, vol. 45, pp. 9804-9815 (2012).
S. Abele et al., "Cationic and Zwitterionic Polymerizable Surfactants: Quaternary Ammonium Dialkyl Maleates 1. Synthesis and Characterization," Langmuir, vol. 15, pp. 1033-1044 (1999).
H. Liu et al., "Zwitterionic copolymer-based and hydrogen bonding-strengthened self-healing hydrogel," RSC Adv., vol. 5, pp. 33083-33088 (2015).
D. Kratzer et al., "A Synthetic Route to Sulfobetaine Methacrylates with Varying Charge Distance," Eur. J. Org. Chem., vol. 2014, pp. 8064-8071 (2014).
H. Tremblay et al., "One-pot synthesis of polyunsaturated fatty acid amides with anti-proliferative properties," Bioorg. Med. Chem. Lett., vol. 24, pp. 5635-5638 (2014).
N.N. Gandhi, "Applications of Lipase," JAOCS, vol. 74, pp. 621-634 (1997).
Int'l Search Report and Written Opinion issued in Int'l Application No. PCT/US2015/055258.

* cited by examiner

HETEROCYCLIC AMPHOTERIC COMPOUNDS

CROSS-REFERENCE TO RELATED APPLICATION

This application is a division of application Ser. No. 14/518,517 filed on Oct. 20, 2014; the entire content of which is hereby incorporated by reference.

PARTIES TO JOINT RESEARCH AGREEMENT

Inventions disclosed or claimed herein were made pursuant to a Joint Research Agreement between Eastman Chemical Company and Johnson & Johnson Consumer & Personal Products Worldwide, a division of Johnson & Johnson Consumer Companies Inc.

FIELD OF THE INVENTION

The invention generally relates to heterocyclic amphoteric compounds. More particularly, the invention relates to heterocyclic quaternary ammonium carboxylates, compositions of such compounds, uses of such compounds, and processes for making them.

BACKGROUND OF THE INVENTION

There is an increasing industrial and societal need for safer and more environmentally-friendly ingredients and methods for preparing those ingredients. In particular, it is highly desirable to provide methods that reduce or eliminate the use of irritating or allergenic starting materials, that employ biocompatible reagents, and that optimally use starting materials derived from a natural source or are "nature-equivalent." This is of urgent interest in consumer-facing industries, such as personal and household care.

One class of materials that may be approached in a "greener" manner is surfactants. Specifically, there is a need for new amphoteric surfactants that avoid using irritating or allergenic starting materials and that are made in a more environmentally-friendly manner.

Amphoteric (or zwitterionic) surfactants are used throughout the personal and household care industries. They are classified as specialty co-surfactants that complement the performance of primary surfactants. These co-surfactants also increase the mildness of the formulation by reducing irritation associated with purely ionic surfactants.

The most common zwitterionic surfactants are amido-amine based materials produced by a multi-step process from coconut or palm kernel oil and N,N-dimethylamino-3-propylamine (DMAPA). Various patents (U.S. Pat. No. 3,280,179; U.S. Pat. No. 4,259,191) and publications (Parris et al., *J. Am. Oil Chem. Soc.*, Vol. 54, pp. 294-296 (1977)) detail commonly used preparation methods for these types of materials. The processes generally involve the amidation of fatty acids with DMAPA at high temperatures (150-175° C.). The intermediate fatty amino-amide is then reacted with a hydrophilic species, e.g., sodium chloroacetate, to yield the betaine.

These processes have several drawbacks. For example, typical amidation processes require high temperatures for conversion and distillation to remove unreacted starting materials. These high reaction temperatures can generate by-products and impart color to the products, requiring additional steps to remove the by-products and the color.

Moreover, DMAPA is a known sensitizer, as is the corresponding amido-amine. Both are found in trace quantities in the final formulation.

Thus, there is a need for amphoteric/zwitterionic surfactants that can be prepared under milder conditions without the use of DMAPA or a DMAPA amide and that can retain or improve the performance properties of traditional zwitterionic surfactants.

The present invention addresses this need as well as others, which will become apparent from the following description and the appended claims.

SUMMARY OF THE INVENTION

The invention is as set forth in the appended claims.

Briefly, in one aspect, the present invention provides a compound having the formula 1:

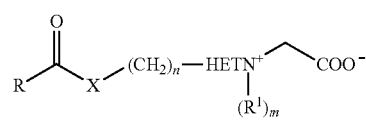

wherein

R is a $C_3$-$C_{23}$ hydrocarbyl group;

$R^1$ is a $C_1$-$C_8$ hydrocarbyl group;

HETN is a heterocyclic group selected from piperidine, pyridine, pyrollidine, quinoline, tetrahydroquinoline, indole, indoline, octahydroindole, acridine, octahydroacridine, and tetradecahydroacridine;

X is O or NH;

n is 0 or 1; and m is 0 or 1 and is chosen to afford a quaternary heterocyclic nitrogen.

In another aspect, the present invention provides a mixture comprising at least two compounds having the formula 1. The at least two compounds have at least one different R substituent.

In another aspect, the present invention provides a process for preparing the compound of formula 1. The process comprises:

(a) contacting an acid or ester of formula 2 with a heterocyclic alcohol of formula 3 or a heterocyclic amine of formula 4:

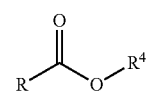

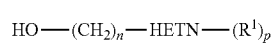

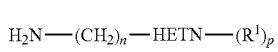

in the presence of an enzyme at conditions effective to form an intermediate of formula 5:

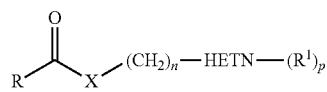

wherein

R, R¹, X, HETN, and n are as defined above,

R⁴ is hydrogen or a $C_1$-$C_6$ alkyl group, and p is 0 or 1 and is chosen to afford a tertiary heterocyclic amine;

(b) contacting the intermediate of formula 5 with an acetic acid alkylating agent at conditions effective to form the compound of formula 1.

In yet another aspect, the present invention provides a process for preparing a mixture comprising at least two compounds having the formula 1 wherein the at least two compounds have different R substituents. The process comprises:

(a) contacting a mixture comprising at least two acids or esters of formula 2 with a heterocyclic alcohol of formula 3 or a heterocyclic amine of formula 4:

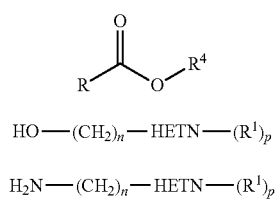

2

HO—$(CH_2)_n$—HETN—$(R^1)_p$   3

$H_2N$—$(CH_2)_n$—HETN—$(R^1)_p$   4 in the presence of an enzyme at conditions effective to form at least two intermediates of formula 5:

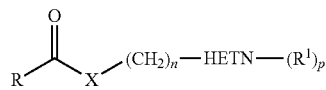

5 wherein

R, R¹, X, HETN, and n are as defined above,

R⁴ is hydrogen or a $C_1$-$C_6$ alkyl group, and p is 0 or 1 and is chosen to afford a tertiary heterocyclic amine, the at least two acids or esters of the formula 2 have different R substituents, and the at least two intermediates of the formula 5 have different R substituents; and (b) contacting the intermediates of the formula 5 with an acetic acid alkylating agent at conditions effective to form the mixture of at least two compounds of the formula 1.

DETAILED DESCRIPTION OF THE INVENTION

In one aspect, the present invention provides a series of heterocyclic amphoteric compounds having the formula 1:

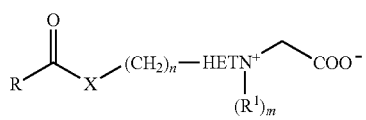

1 wherein

R is a $C_3$-$C_{23}$ hydrocarbyl group;

R¹ is a $C_1$-$C_8$ hydrocarbyl group;

HETN is a heterocyclic group selected from piperidine, pyridine, pyrollidine, quinoline, tetrahydroquinoline, indole, indoline, octahydroindole, acridine, octahydroacridine, and tetradecahydroacridine;

X is O or NH;

n is 0 or 1; and m is 0 or 1 and is chosen to afford a quaternary heterocyclic nitrogen.

As used herein, the term "hydrocarbyl" refers to a monovalent hydrocarbon group. The term includes groups such as alkyls, alkenes, alkynes, aryls, and cycloalkyls.

The hydrocarbyl group of R may be substituted or unsubstituted; branched or straight-chain; and saturated, mono-unsaturated, or poly-unsaturated. The hydrocarbyl group of R may also be a substituted or unsubstituted $C_3$-$C_8$ cycloalkyl group.

In a preferred embodiment, R is selected from substituted or unsubstituted, branched- or straight-chain, saturated $C_5$-$C_{19}$ alkyl; substituted or unsubstituted, branched- or straight-chain $C_5$-$C_{17}$ alkenyl; substituted or unsubstituted, branched- or straight-chain $C_5$-$C_{17}$ dienyl; and substituted or unsubstituted $C_3$-$C_8$ cycloalkyl.

The hydrocarbyl group of R may be substituted with one to five substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

As used herein, the terms "$C_1$-$C_6$ alkoxy," "$C_2$-$C_6$ alkoxycarbonyl," and "$C_2$-$C_6$ alkanoyloxy" are used to denote radicals corresponding to the structures —$OR^2$, —$CO_2R^2$, and —$OCOR^2$, respectively, where $R^2$ is a substituted or unsubstituted $C_1$-$C_6$ alkyl group.

As used herein, the terms "$C_1$-$C_{15}$ aminocarbonyl" and "$C_1$-$C_{15}$ amido" are used to denote radicals corresponding to the structures —$NHCOR^3$ and —$CONHR^3$, respectively, where $R^3$ is a substituted or unsubstituted $C_1$-$C_{15}$ alkyl group.

As used herein, the term "$C_3$-$C_8$ cycloalkyl" is used to denote a saturated, carbocyclic hydrocarbon radical having three to eight carbon atoms.

The hydrocarbyl group of R¹ may be branched or straight-chain; substituted or unsubstituted; and saturated, mono-unsaturated, or poly-unsaturated. In one embodiment, R¹ is selected from substituted or unsubstituted, straight-chain or branched $C_1$-$C_6$ alkyl or alkenyl groups. In another embodiment, R¹ is selected from substituted or unsubstituted $C_3$-$C_8$ cycloalkyl groups.

In a preferred embodiment, R¹ is selected from branched or straight-chain $C_1$-$C_6$ alkyl groups.

The hydrocarbyl radicals of R¹ may be substituted with one to three substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

HETN represents a heterocyclic amino group. HETN may be selected from piperidine, pyridine, pyrollidine, quinoline, tetrahydroquinoline, indole, indoline, octahydroindole, acridine, octahydroacridine, and tetradecahydroacridine. When HETN is aromatic, such as in the case of pyridine, m is 0, since R¹ is not needed to afford a quaternary nitrogen in the HETN group. Conversely, when HETN is aliphatic, such as in the case of piperidine, m is 1, since R¹ would be needed to afford a quaternary nitrogen in the HETN group.

Preferred HETN groups include piperidine, pyridine, and pyrollidine.

The $RC(O)X(CH_2)_n$— moiety in formula 1 may be attached to any carbon atom on the heterocyclic group HETN. Preferred positions include the 3- or the 4-position of the heterocyclic ring.

Examples of the compounds of the invention include those represented by the formula 1 where R is selected from the group consisting of $C_5$-$C_{19}$ alkyl, $C_5$-$C_{17}$ alkenyl, $C_5$-$C_{17}$ dienyl, and $C_3$-$C_8$ cycloalkyl; $R^1$ is a $C_1$-$C_6$ alkyl group; HETN is selected from the group consisting of piperidine, pyridine, and pyrollidine; X is O or NH; n is 0 or 1; and m is 0 or 1 and is chosen to afford a quaternary heterocyclic nitrogen.

Other examples of the compounds of the invention include those represented by the formula 1 where RCO— is octanoyl, decanoyl, lauroyl, myristoyl, or a $C_6$ to $C_{20}$ acyl radical derived from coconut oil, hydrogenated coconut oil, or hydrogenated and/or fractionated coconut oil fatty acids; $R^1$ is methyl; HETN is a 3-piperidine group or a 4-piperidine group; X is O or NH; n is 0 or 1; and m is 1. In one embodiment, RCO— in this set of exemplary compounds is lauroyl.

Additional examples of the compounds of the invention include those represented by the formula 1 where RCO— is octanoyl, decanoyl, lauroyl, myristoyl, or a $C_6$ to $C_{20}$ acyl radical derived from coconut oil, hydrogenated coconut oil, or hydrogenated and/or fractionated coconut oil fatty acids; HETN is a 3-pyridine group or a 4-pyridine group; X is O or NH; n is 0 or 1; and m is 0. In one embodiment, RCO— in this set of exemplary compounds is lauroyl.

Specific examples of the compounds of the formula 1 include (4-cocoyloxy-1-methylpiperidinium-1-yl)acetate, (3-cocoyloxymethyl-1-methylpiperidinium-1-yl)acetate, (4-cocoyloxymethyl-1-methylpiperidinium-1yl)acetate, (4-lauroyloxy-1-methylpiperidinium-1-yl)acetate, (3-lauroyloxymethyl-1-methylpiperidinium-1-yl)acetate, 4-(lauroyloxymethylpyridinium-1-yl)acetate, 4-(lauramidomethylpyridinium-1-yl)acetate, and (4-lauramido-1-methylpiperidinium-1-yl)acetate.

In various embodiments of the invention, the "$C_6$ to $C_{20}$ acyl radical" may be derived from coconut oil, hydrogenated coconut oil, or hydrogenated and/or fractionated coconut oil fatty acids. In which case, the resulting product may be a mixture of two or more compounds of the formula 1 where each compound has a different R substituent. For example, the "$C_6$ to $C_{20}$ acyl radical" may be derived from hydrogenated and stripped/fractionated coconut fatty acids. Coconut fatty acids typically include a mixture of fatty acids, such as $C_8$, $C_{10}$, $C_{12}$, $C_{14}$, $C_{16}$, and $C_{18}$ fatty acids. The fatty acids may be saturated, mono-unsaturated, or poly-unsaturated. The mixture may be hydrogenated to increase its melting point. In addition, the mixture may be stripped, for example, of the medium-chain fatty acids, such as $C_8$ and $C_{10}$ fatty acids, to yield a fraction of predominately long-chain fatty acids, such as $C_{12}$-$C_{18}$ fatty acids. These fractions (either the medium-chain or the long-chain, for example) may be used to produce the compounds of the invention. When such fractions are used, the reaction product would include a mixture of the compounds of the formula 1 where some compounds may have, for example, a $C_{12}$ acyl radical substituent while other compounds may have a $C_{14}$ acyl radical substituent, etc.

Thus, in another aspect, the present invention provides a mixture comprising at least two compounds having the formula 1:

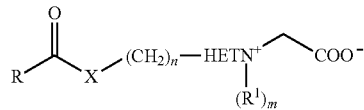

wherein
R is a $C_{3-23}$ hydrocarbyl group;
$R^1$ is a $C_1$-$C_8$ hydrocarbyl group;
HETN is a heterocyclic group selected from piperidine, pyridine, pyrollidine, quinoline, tetrahydroquinoline, indole, indoline, octahydroindole, acridine, octahydroacridine, and tetradecahydroacridine;
X is O or NH;
n is 0 or 1; and
m is 0 or 1 and is chosen to afford a quaternary heterocyclic nitrogen.

The at least two compounds have at least one different R substituent. In other words, the at least two compounds have different R substituents.

Examples of the compounds in the mixture according to the invention include those represented by the formula 1 where RCO— is selected from octanoyl, decanoyl, lauroyl, myristoyl, and a $C_6$ to $C_{20}$ acyl radical derived from coconut oil, hydrogenated coconut oil, or hydrogenated and/or fractionated coconut oil fatty acids; $R^1$ is methyl; HETN is a 3-piperidine group or a 4-piperidine group; X is O or NH; n is 0 or 1; and m is 1. In one embodiment, the at least two compounds have different R substituents selected from $C_6$ to $C_{20}$ acyl radicals derived from coconut oil, hydrogenated coconut oil, or hydrogenated and/or fractionated coconut oil fatty acids. In another embodiment, RCO— in one compound is lauroyl and RCO— in another compound is myristoyl. In yet another embodiment, RCO— in one compound is octanoyl and RCO— in another compound is decanoyl.

Other examples of the compounds in the mixture according to the invention include those represented by the formula 1 where RCO— is selected from octanoyl, decanoyl, lauroyl, myristoyl, and a $C_6$ to $C_{20}$ acyl radical derived from coconut oil, hydrogenated coconut oil, or hydrogenated and/or fractionated coconut oil fatty acids; HETN is a 3-pyridine group or a 4-pyridine group; X is O or NH; n is 0 or 1; and m is 0. In one embodiment, the at least two compounds have different R substituents selected from $C_6$ to $C_{20}$ acyl radicals derived from coconut oil, hydrogenated coconut oil, or hydrogenated and/or fractionated coconut oil fatty acids. In another embodiment, RCO— in one compound is lauroyl and RCO— in another compound is myristoyl. In yet another embodiment, RCO— in one compound is octanoyl and RCO— in another compound is decanoyl.

In another aspect, the present invention provides a process for preparing a compound of the formula 1. The process may be used to prepare any of the compounds of the formula 1 described herein. The process comprises:

(a) contacting an acid or ester of formula 2 with a heterocyclic alcohol of formula 3 or a heterocyclic amine of formula 4:

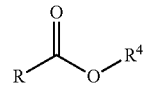

-continued

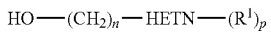   3

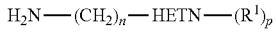   4 in the presence of an enzyme at conditions effective to form an intermediate of formula 5:

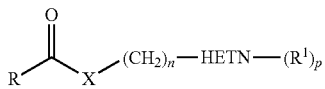   5 wherein

R, $R^1$, X, HETN, and n are as defined herein above, $R^4$ is hydrogen or a $C_1$-$C_6$ alkyl group, and p is 0 or 1 and is chosen to afford a tertiary heterocyclic amine; and (b) contacting the intermediate of formula 5 with an acetic acid alkylating agent at conditions effective to form the compound of formula 1.

The $C_1$-$C_6$ alkyl group of $R^4$ may be branched or straight-chain.

The carboxylic acid or ester of the formula 2 may be obtained commercially or may be produced by any practical method, including the hydrolysis or solvolysis of triglycerides in the presence of water or a lower alcohol and a base, acid, or enzyme catalyst, as is known in the art. The preferred lower alcohols are $C_1$-$C_4$ alcohols, such as methanol, ethanol, 1-propanol, 2-propanol, 1-butanol, 2-butanol, and isobutanol.

Likewise, the heterocyclic alcohol of the formula 3 and the heterocyclic amine of the formula 4 may be obtained commercially or may be produced by methods known in the art.

The first step of the process involves reacting the heterocyclic alcohol of the formula 3 or the heterocyclic amine of the formula 4 with the acid or ester of the formula 2 in the presence of an enzyme to form the desired intermediate of the formula 5.

The enzymatic reaction of step (a) may be carried out without an added solvent or in the presence of an inert solvent. Examples of inert solvents include cyclic or acyclic ether solvents (such as diethyl ether, diisopropyl ether, tert-butyl methyl ether, and tetrahydrofuran), aromatic hydrocarbons (such as benzene, toluene, and xylene), aliphatic or alicyclic, saturated or unsaturated hydrocarbons (such as hexane, heptane, cyclohexane, and limonene), halogenated hydrocarbons (such as dichloromethane, dichloroethane, dibromoethane, tetrachloroethylene, and chlorobenzene), polar aprotic solvents (such as acetonitrile, dimethyl formamide, and dimethyl sulfoxide), and mixtures thereof.

In one embodiment, the enzymatic reaction is carried out in the absence of an added solvent.

In another embodiment, the enzymatic reaction is carried out in the presence of one or more aromatic or aliphatic hydrocarbons as the solvent.

The enzymatic reaction may be carried out at a temperature from about −100° C. to the boiling point of the solvent (if employed), preferably from about 20 to 100° C., and more preferably from 50 to 90° C. The amount of the alcohol 3 or amine 4 may be from 0.85 to 20 equivalents, based on the fatty acid or ester 2, preferably from 1 to 10 equivalents, and more preferably from 1 to 1.5 equivalents.

Step (a) in the process of the invention is desirably carried out in the presence of an enzyme effective to react the fatty acid or ester 2 with the alcohol 3 or amine 4 to form the intermediate compound of the formula 5. Effective enzymes for this reaction include lipases. Examples of these enzymes include, but are not limited to, Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL IM, Novozyme 435 (lipase from *Candida antarctica* immobilized on acrylic resin), and *Candida antarctica* lipase B immobilized on a porous fluoropolymer support as described in US 2012/0040395 A1. Immobilized enzymes have the advantage of being easily removed from the product and re-used.

The enzymatic reaction may be carried out with or without in situ water or alcohol by-product removal. The water or alcohol by-product can be removed by any known technique, such as chemically via an alcohol or water absorbent (e.g., molecular sieves) or by physical separation (e.g., evaporation). This by-product removal is preferably performed by evaporation, either by purging the reaction mixture with an inert gas such as nitrogen, argon, or helium, or by performing the reaction at reduced pressures, or both, as these conditions can afford >98% conversion of the fatty acid or ester 2 to the intermediate 5. The preferred pressure for carrying out the reaction ranges from 1 Torr (133.3 Pa) to ambient pressure, more preferably from 10 Torr (1,333 Pa) to ambient pressure, and most preferably from 50 Torr (6,665 Pa) to ambient pressure. Any organic solvent that is included in this step may or may not be removed along with the alcohol or water. Upon completion of the reaction in step (a), the intermediate 5 of the process may be isolated using methods known to those of skill in the art, e.g., extraction, filtration, or crystallization.

The second step in the process to generate the final product of the formula 1 involves reacting the intermediate compound of the formula 5 with an acetic acid alkylating agent. The acetic acid alkylating agent is typically an acetic acid derivative substituted at the 2-position with a leaving group. The leaving group is preferably a halide (e.g., fluoride, chloride, bromide, etc.). The acetic acid derivative is preferably neutralized either prior to use or in situ with a base such as sodium hydroxide, potassium hydroxide, sodium carbonate, potassium carbonate, sodium bicarbonate, or potassium bicarbonate. The preferred acetic acid alkylating agent is sodium chloroacetate or chloroacetic acid neutralized in situ with sodium hydroxide.

This step (b) may also be carried out without an added solvent or in the presence of a solvent. Examples of solvents include water, alcohols and diols (such as methanol, ethanol, 1-propanol, 2-propanol, 1-butanol, 2-butanol, isobutanol, tert-butanol, tert-pentanol, ethylene glycol, 1,2-propanediol, and 1,3-propanediol), cyclic or acyclic ethers (such as diethyl ether, diisopropyl ether, tert-butyl methyl ether, and tetrahydrofuran), ether-alcohols (such as 2-methoxyethanol, 1-methoxy-2-propanol, ethylene glycol monobutyl ether, diethylene glycol monoethyl ether, diethylene glycol monopropyl ether, and diethylene glycol monobutyl ether), aromatic hydrocarbons (such as benzene, toluene, and xylene), aliphatic or alicyclic, saturated or unsaturated hydrocarbons (such as hexane, heptane, cyclohexane, and limonene), halogenated hydrocarbons (such as dichloromethane, dichloroethane, dibromoethane, tetrachloroethylene, and chlorobenzene), polar aprotic solvents (such as acetonitrile, dimethyl formamide, and dimethyl sulfoxide), and mixtures thereof. The preferred solvents include water, $C_2$-$C_5$ alcohols, ether-alcohols, and mixtures thereof.

The second step may be carried out at a temperature from about −100° C. to the boiling point of the solvent (if employed), preferably from about 25 to 150° C., more preferably from 50 to 150° C., and most preferably from 50 to 125° C.

The reaction in the second step may be carried out over a wide range of pressures. For example, the pressure may range from atmospheric to super-atmospheric, e.g., 5 atmospheres or higher.

The amount of acetic acid alkylating agent used is not particularly limiting. For example, the acetic acid alkylating agent may be used in an amount ranging from 0.75 to 20 equivalents based on the intermediate 5, preferably from 1 to 10 equivalents, and more preferably from 1 to 1.5 equivalents.

Optionally, a base (in excess of what is needed to neutralize the acetic acid derivative) is included in the reaction mixture of step (b). If included, the base may be chosen from metal hydroxides, metal carbonates, and metal bicarbonates. Preferred bases include sodium carbonate and sodium bicarbonate. The amount of base used can be from 0 molar equivalents to 1 molar equivalent, based on the intermediate of the formula 5. The preferred amount is a quantity sufficient to keep the reaction mixture slightly basic, generally a pH of 7.2 or greater.

Upon completion of the reaction in step (b), the intermediate 5 and the product 1 of the process may be isolated using methods known to those of skill in the art, e.g., extraction, filtration, or crystallization.

The process of the invention may be used to prepare a mixture of two or more compounds of the formula 1. In particular, the process may be used to prepare any mixture of two or more compounds of the formula 1 described herein. As noted above, the two or more compounds of the formula 1 would have different R substituents. If desired, a mixture of two or more carboxylic acids or esters of the formula 2, with different R substituents, may be employed in the enzymatic reaction step (a). Such mixtures may be derived from, for example, coconut oil, hydrogenated coconut oil, or hydrogenated and/or fractionated coconut oil fatty acids. The enzymatic reaction step (a) would yield a mixture of two or more intermediates of the formula 5, wherein the intermediates 5 would have different R substituents. The mixture of intermediates 5 may then be reacted with the acetic acid alkylating agent to produce the mixture of two or more compounds of the formula 1.

The heterocyclic amphoteric compounds of the formula 1 are particularly useful as surfactants. Thus, another aspect of the present invention relates to compositions of matter comprising one or more compounds of the formula 1 as surfactants. The compositions may contain from 0.001 to 20 weight percent of the compounds of the formula 1.

In particular, the heterocyclic amphoteric compounds of the invention possess both hydrophilic and hydrophobic regions, making them useful as surfactants in a number of formulated product applications, including personal care products, such as skin care, hair care, and other cosmetic products; household and industrial surface cleaners; laundry products; dish cleaners; disinfectants; metal working compositions; rust inhibitors; lubricants; oil field products; oil dispersants; agrochemicals; and dye dispersions. The heterocyclic amphoteric compounds can also be used as emulsifiers and thickening agents in emulsions. The heterocyclic amphoteric compounds can be formulated into products as primary or secondary surface-active agents. Although their primary use is as cleansing and foaming agents, the heterocyclic amphoteric compounds can also used for their antistatic, viscosity-controlling, emulsifying, wetting, and dispersing properties.

Such formulated products can contain from about 0.001 weight % to about 20 weight %, from about 0.01 weight % to about 15 weight %, or even from about 0.1 weight % to about 10 weight % of the heterocyclic amphoteric compounds.

The formulated products of the invention may include other surfactants in addition to the heterocyclic amphoteric compounds. These other surfactants can include anionic surfactants (such as alcohol ether sulfates, linear alkylbenzene sulfonates, and acyl isethionates), cationic surfactants (such as quaternary ammonium salts, amine oxides, and ester quats), amphoteric surfactants (such as betaines, amidobetaines, ester betaines, and amphoacetates), and nonionic surfactants (such as alky polyglycosides, alcohol ethoxylates, and fatty alcanol amides). Such ingredients are known to those of skill in the art.

As noted, the formulated products of the invention can be cosmetic, skin, and hair care compositions. Those compositions may contain skin conditioning ingredients or cosmetically acceptable carriers in addition to the heterocyclic amphoteric compounds.

Such skin care ingredients/carriers include retinol, retinyl esters, tetronic acid, tetronic acid derivatives, hydroquinone, kojic acid, gallic acid, arbutin, α-hydroxy acids, niacinamide, pyridoxine, ascorbic acid, vitamin E and derivatives, aloe, salicylic acid, benzoyl peroxide, witch hazel, caffeine, zinc pyrithione, and fatty acid esters of ascorbic acid. Other skin care ingredients and carriers are known to those of skill in the art and may be used in the compositions of the invention.

Additional ingredients that may be included in these formulations include conditioning agents (such as polyquaterniums and panthenol), pearlizing agents (such as glycol distearate, distearyl ether, and mica), UV filters (such as octocrylene, octyl methoxycinnamate, benzophenone-4, titanium dioxide, and zinc oxide), exfoliation additives (such as apricot seeds, walnut shells, polymer beads, and pumice), silicones (such as dimethicone, cyclomethicone, and amodimethicone), moisturizing agents (such as petrolatum, sunflower oil, fatty alcohols, and shea butter), foam stabilizers (such as cocamide MEA and cocamide DEA), anti-bacterial agents such as triclosan, humectants such as glycerin, thickening agents (such as guar, sodium chloride, and carbomer), hair and skin damage repair agents (such as proteins, hydrolyzed proteins, and hydrolyzed collagen), and foam boosters such as cocamide MIPA. Such additional ingredients are known to those of skill in the art and may be used in the compositions of the invention.

Many personal care preparations are known in the art. They typically include acceptable carriers (such as water, oils and/or alcohols), emollients (such as olive oil, hydrocarbon oils and waxes, silicone oils, other vegetable, animal or marine fats or oils, glyceride derivatives, fatty acids or fatty acid esters), alcohols or alcohol ethers, lecithin, lanolin and derivatives, polyhydric alcohols or esters, wax esters, sterols, phospholipids, and the like. These same general ingredients can be formulated into liquids (such as liquid soaps, shampoos, or body washes), creams, lotions, gels, or into solid sticks by using different proportions of the ingredients and/or by inclusion of thickening agents such as gums or other forms of hydrophilic colloids. All such preparations may include the heterocyclic amphoteric compounds of the invention.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Example 1

Preparation of Methyl Cocoate

To a jar was added potassium hydroxide (1 g) and methanol (25 g). The solution was stirred for 1 hour. To a separate jar was added coconut oil (100 g). The solid was heated to a melt, and the KOH/MeOH solution was added, and the mixture was stirred overnight. The mixture was transferred to a separatory funnel and allowed to separate. The bottom/glycerol layer was removed. The top layer was filtered to afford a pale yellow oil (100 g). $^1$H NMR (300 MHz, CDCl$_3$) δ 3.65 (s, 3H), 2.28 (t, 2H), 1.60 (m, 2H), 1.24 (s, 16H), 0.86 (t, 3H).

Example 2

Preparation of 1-methyl-4-piperidyl cocoate

To a 250-mL round bottom flask with a magnetic stir bar was added methyl cocoate (25 g, 117 mmol), 4-hydroxy-N-methylpiperidine (17.46 g, 152 mmol), heptane (10 mL), and Novozyme 435 (2.50 g). A Dean-Stark trap was placed onto the flask, and vacuum was applied to the system. The mixture was heated to 65° C. The heptane azeotrope was utilized to remove methanol by reducing the pressure until the azeotrope distilled overhead into the Dean-Stark trap to return the heptane to the reaction vessel. After 1.5 hrs, the reaction was stopped. After the mixture was cooled to ambient temperature, Novozyme 435 was recovered by filtration. After heating to 65° C., nitrogen was bubbled through the mixture to remove any unreacted 4-hydroxy-N-methylpiperidine. $^1$H NMR analysis indicated 98% conversion to the product, which was isolated as a yellow oil (29.57 g). $^1$H NMR (300 MHz, CDCl$_3$) δ 4.78 (m, 1H), 2.66 (m, 2H), 2.32-2.22 (m, 7H); 1.95-1.86 (m, 2H); 1.77-1.58 (m, 4H); 1.38-1.25 (m, 18H), 0.88 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.7 min.

Example 3

Preparation of (4-cocoyloxy-1-methylpiperidinium-1-yl)acetate

To a 100-mL round bottom flask was added 1-methyl-4-piperidinyl cocoate (10.0 g, 32.1 mmol), sodium chloroacetate (4.30 g, 36.9 mmol), and sodium bicarbonate (540 mg, 6.42 mmol). Water (12.1 mL) and isopropanol (12.1 mL) were then added. The mixture was heated to 80° C. and stirred at this temperature for 19.5 hours. After this time, LC analysis indicated 98.3% conversion. After cooling to ambient temperature, the volatiles were removed at reduced pressure. Enough water was added back to the flask to obtain ca. 38.75 g of the total mixture. The homogenous mixture was heated to 60° C. while sparging the headspace of the flask with 1000 mL/min of nitrogen. Over time, additional water was added to the solution to maintain 38.75 g of the total mass. After 5 hrs, isopropanol was not observed in the $^1$H NMR. After cooling to ambient temperature, the mixture was filtered through 1-micron filter paper. The resulting solution was determined to be 28.3 wt % (4-cocoyloxy-1-methylpiperidinium-1-yl)acetate in water by internal standard $^1$H NMR analysis. $^1$H NMR analysis was consistent with the product structure. HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 5.3 min.

Example 4

Preparation of 3-cocoyloxymethyl-N-methylpiperidine

To a 250-mL round bottom flask with a magnetic stir bar was added methyl cocoate (69.0 g, 322 mmol), 3-hydroxymethyl-1-methylpiperidine (49.89 g, 386 mmol), and Novozyme 435 (10.0 g). The flask was fitted with a septum, and a needle was inserted to vent. Nitrogen was bubbled subsurface at a rate sufficient to mix the contents. The mixture was heated to 65° C. After 12 hrs, the sparge rate was increased. At 19.5 hrs, $^1$H NMR analysis indicated that the reaction was complete. After filtration, the mixture was taken up in Et$_2$O (750 mL) and subsequently washed with water (250 mL×2). The organics were dried with Na$_2$SO$_4$. After filtration, the volatiles were removed under reduced pressure to afford the product as a pale yellow oil (91.67 g). $^1$H NMR (300 MHz, CDCl$_3$) δ 3.98 (m, 1H), 3.86 (m, 1H), 2.80 (m, 2H), 2.28 (t, 2H), 2.25 (s, 3H), 2.03-1.82 (m, 2H), 1.72-1.55 (m, 5H), 1.33-1.18 (m, 18H), 0.87 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 5.1 min.

Example 5

Preparation of (3-cocoyloxymethyl-1-methylpiperidinium-1-yl)acetate

To a 100-mL round bottom flask was added 3-cocoyloxymethyl-1-methylpiperidine (10.0 g, 30.8 mmol), sodium chloroacetate (4.12 g, 35.4 mmol), and sodium bicarbonate (517 mg, 6.16 mmol). Water (12.1 mL) and isopropanol (12.1 mL) were then added. The mixture was heated to 80° C. and stirred at this temperature for 25 hours. After this time, LC analysis indicated 98.0% conversion. The resulting mixture weighed 33.9 g and was ca. 31.6 wt % (3-cocoyloxymethyl-1-methylpiperidinium-1-yl)acetate in water:isopropanol. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.6 min.

Example 6

Preparation of (1-methylpiperidin-4-yl)methyl cocoate

To a 250-mL round bottom flask was added methyl cocoate (50 g, 233 mmol), 4-hydroxymethyl-N-methylpiperidine (33.2 g, 257 mmol), and Novozyme 435 (5.0 g). The flask was fitted with a septum, and a needle was inserted to vent. Nitrogen was bubbled subsurface at a rate sufficient to mix the contents. The reaction mixture was heated to 50° C. After approximately 15 hours, $^1$H NMR analysis indicated that the reaction was complete. The reaction mixture was allowed to cool. The Novozyme 435 was removed by filtration. The material was taken up in diethyl ether (250 mL) and subsequently washed with water (250 mL×2). After drying with $Na_2SO_4$, the mixture was filtered and concentrated. After dissolving in small amount of dichloromethane, the mixture was filtered through a short plug of MAGNESOL filter powder and concentrated to afford the product as a pale yellow oil (57.89 g). $^1$H NMR (300 MHz, $CDCl_3$) δ 3.93 (d, 2H), 2.86 (m, 2H), 2.32-2.27 (m, 5H), 1.91 (t, 3H), 1.73-1.56 (m, 5H), 1.41-1.23 (m, 19H), 0.88 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.1 min.

Example 7

Preparation of (4-cocoyloxymethyl-1-methylpiperidinium-1yl)acetate

To a 100-mL round bottom flask was added (1-methylpiperidin-4-yl)methyl cocoate (10.0 g, 30.7 mmol), sodium chloroacetate (4.11 g, 35.3 mmol), and sodium bicarbonate (520 mg, 6.14 mmol). Water (12.1 mL) and isopropanol (12.1 mL) were then added. The mixture was heated to 80° C. and stirred at this temperature for 18.75 hours. After this time, HPLC analysis indicated 99.4% conversion. After cooling to ambient temperature, the volatiles were removed at reduced pressure. Enough water was added back to the flask to obtain ca. 38.5 g of the total mixture. The homogenous mixture was heated to 60° C. while sparging the headspace of the flask with 1000 mL/min of nitrogen. Over time, additional water was added to the solution to maintain 38.5 g of the total mass. After 5 hrs, isopropanol was not observed in the $^1$H NMR. After cooling to ambient temperature, the mixture was filtered through 1-micron filter paper. The resulting mixture was ca. 36.4 wt % (4-cocoyloxymethyl-1-methylpiperidinium-1yl)acetate in water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.6 min.

Example 8

Preparation of 1-methyl-4-piperidinyl laurate

To a 250-mL round bottom flask with a magnetic stir bar was added methyl laurate (25 g, 117 mmol), 4-hydroxy-N-methylpiperidine (17.46 g, 152 mmol), heptane (10 mL), and Novozym 435 (2.50 g). A Dean-Stark trap was placed onto the flask, and the reaction was placed under vacuum. The mixture was heated to 65° C. The heptane azeotrope was utilized to remove methanol by reducing the pressure until the azeotrope distilled overhead into the Dean-Stark trap to return the heptane to the reaction vessel. After 3 hrs, GC analysis indicated 98.7% conversion. The reaction was allowed to cool to ambient temperature. Novozym 425 was recovered by filtration. The mixture was taken up in diethyl ether (100 mL) and washed with water (100 mL). The organics were dried with $Na_2SO_4$. After filtration, the volatiles were removed under reduced pressure to afford a pale yellow oil that solidified upon standing (32.09 g). $^1$H NMR (300 MHz, $CDCl_3$) δ 4.78 (m, 1H), 2.65 (m, 2H), 2.32-2.22 (m, 7H); 1.95-1.85 (m, 3H); 1.77-1.57 (m, 4H); 1.35-1.23 (m, 17H), 0.88 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.6 min.

Example 9

Preparation of (4-lauroyloxy-1-methylpiperidinium-1-yl)acetate

To a 150-mL round bottom flask was added 1-methyl-4-piperidinyl laurate (5.00 g, 16.1 mmol), sodium chloroacetate (2.52 g, 21.7 mmol), and sodium bicarbonate (270 mg, 3.21 mmol). Water (2.4 mL) and isopropanol (9.7 mL) were then added. The mixture was heated to 80° C. and stirred at this temperature for 21 hours, at which time HPLC analysis indicated 99.2% conversion. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.0 min.

Example 10

Preparation of (1-methylpiperidin-3-yl)methyl laurate

To a 3-neck, 2-L round bottom flask fitted with an overhead stirrer and a Dean-Stark trap with cold-finger condenser was added methyl laurate (302 g, 1.41 mol) and 3-hydroxymethyl-1-methylpiperidine (200 g, 1.56 mol). Novozym 435 (30 g) was added, followed by the addition of heptane (120 mL). The internal pressure was reduced to 85 mm Hg and controlled by a vacuum regulator. The mixture was heated to 65° C. After 1.5 hrs, 23 mL of methanol had collected in the Dean-Stark trap. At that point, the reaction was cooled to ambient temperature. The mixture was allowed to stand overnight. The following morning, the pressure was once again reduced to 85 mm Hg, and the mixture was heated to 65° C. The reaction was checked by $^1$H NMR after 5.5 hours. Additional 3-hydroxymethyl-1-methylpiperidine (9.00 g) was added. After 7.5 hrs, the mixture was cooled to ambient temperature. Then additional 3-hydroxymethyl-4-methylpiperidine (17.9 g) was once again added. The pressure was reduced to 65 mm Hg, and the mixture was heated to 65° C. After 5 hrs, the reaction was stopped. The mixture was filtered, and the solids were washed with additional heptane. Heptane (500 mL) was added to the organics, which were then washed with water (1×500 mL). After the layers were separated, the organics were dried with Na$_2$SO$_4$. After filtration, most of the volatiles were removed at reduced pressure. The remaining material was heated to 50° C. and sparged (subsurface) for ca. 24 hrs with nitrogen at 100 mL/min to drive off residual heptane affording the title compound as a pale yellow oil (401.7 g) that was 98.4% pure by $^1$H NMR analysis. $^1$H NMR (300 MHz, CDCl$_3$) δ 3.95 (m, 2H), 2.08 (m, 2H), 2.30 (t, J=9 Hz, 2H), 2.27 (s, 3H) 2.01-1.83 (m, 2H); 1.77-1.56 (m, 8H); 1.37-1.21 (m, 17H), 0.89 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.0 min.

Example 11

Preparation of (3-lauroyloxymethyl-1-methylpiperidinium-1-yl)acetate

To a jacketed 4-L reactor with overheard stirrer was charged 3-lauroyloxymethyl-N-methylpiperidine (694.62 g, 2.13 mol) and sodium chloroacetate (200 g). Water (2220 mL) was then added. After stirring was initiated, the jacket set point was adjusted to 97° C. After 2 hours, the internal temperature stabilized at 88° C. After 5.75 hours, sodium bicarbonate (71.7 g, 850 mmol) was slowly added over a 35-minute period. After gas evolution had mostly ceased, additional sodium chloroacetate (136 g) was added. At 21.75 hours of reaction time, HPLC analysis indicated 99.5% conversion. The resulting pale-yellow solution weighed 3188 g and was 24.4 wt % (3-lauroyloxymethyl-1-methyl-piperidinium-1-yl)acetate in water by internal standard $^1$H NMR. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.3 min.

Example 12

Preparation of (4-pyridinyl)methyl laurate

To a 125-mL round bottom flask with a magnetic stir bar was added methyl laurate (19.6 g, 92 mmol), 4-hydroxymethylpyridine (10.00 g, 92 mmol), and Novozym 435 (2 g).

Heptane was added and the mixture was heated to 50° C. and sparged with subsurface nitrogen. After 4 hrs, GC analysis indicated 66% conversion and after 24 h 94% conversion was observed. The reaction was allowed to proceed for an additional day and then cooled to ambient temperature. The mixture was diluted with heptane and toluene, and the Novozym 435 was removed by filtration and the cake was washed with toluene. The combined filtrate and wash was washed with 1:1 (v:v) methanol:water (30 mL), 3:2 (v:v) 10 vol % aqueous potassium carbonate:methanol, and aqueous sodium chloride. The organics were dried with Na$_2$SO$_4$ and concentrated to afford the product (16.90 g; 63%). $^1$H NMR (300 MHz, dmso-d$_6$) δ 8.54 (dd, 2h, J=4.3, 1.6 Hz); 7.33 (m, 2H); 5.13 (s, 2H); 2.40 (t, 2H, J=7.3 Hz), 1.6-1.4 (m, 2H); 1.22 (m, 20H), 0.84 (t, 3H, J=6.4 Hz).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 7.1 min.

Example 13

Preparation of (4-lauroyloxymethylpyridinium-1-yl)acetate

Sodium chloroacetate (0.440 g; 3.77 mmol; 1.1 equiv.) and sodium bicarbonate (58 mg; 0.69 mmol; 0.2 equiv.) were combined in a 20-mL vial with a magnetic stir bar. Water (1 mL) was added. 4-(Pyridinyl)methyl laurate (1.0 g; 3.43 mmol) was added, followed by 2 mL of isopropanol. The homogeneous mixture was stirred at ambient temperature for 5 days to afford 23% conversion to product. The mixture was then heated to 50° C. for 28 h to afford 78% conversion to 4-(lauroyloxymethylpyridinium-1-yl)acetate.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.95 min.

Example 14

Preparation of (4-pyridinyl)methyl lauramide

To a 125-mL round bottom flask with a magnetic stir bar was added methyl laurate (14.87 g, 69.4 mmol), 4-aminomethylpyridine (7.50 g, 69.4 mmol), and Novozym 435 (1.5 g). Heptane was added and the mixture was heated to 50° C. and sparged with subsurface nitrogen at 500 mL/min. After 5.5 hrs, the material had solidified, and GC analysis indicated 87% conversion of the methyl laurate to product and no apparent aminomethylpyridine remaining. The mixture was diluted with toluene while hot, the Novozym 435 was removed by filtration, and the cake was washed with toluene. The filtrate was cooled to ambient temperature and diluted with heptane to afford a thick yellow slurry. The mixture was filtered, and the solid was washed with heptane and air-dried to afford 4-pyridinylmethyl lauramide (14.75 g; 73%). $^1$H NMR (300 MHz, dmso-d$_6$) δ 8.48 (dd, 2h, J=4.4, 1.6 Hz); 8.40 (t, 1H, J=6.0 Hz); 7.22 (dd, 2H, J=4.4, 0.70 Hz); 4.27 (d, 2H, J=6.0 Hz); 2.15 (t, 2H, J=7.3 Hz), 1.6-1.4 (m, 2H); 1.22 (m, 20H), 0.85 (t, 3H, J=6.9 Hz).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 3.7 min.

Example 15

Preparation of (4-lauramidomethylpyridinium-1-yl)acetate

Sodium chloroacetate (0.441 g; 3.79 mmol; 1.1 equiv.) and sodium bicarbonate (58 mg; 0.69 mmol; 0.2 equiv.) were combined in a 20-mL vial with a magnetic stir bar. Water (1 mL) was added. 4-(Pyridinyl)methyl lauramide (1.0 g; 3.44 mmol) was added, followed by 2 mL of isopropanol. The mixture was very thick so an additional 1 mL of isopropanol was added. The resulting mixture was stirred at ambient temperature for 5 days to afford 69% conversion to product. The mixture was then heated to 50° C. for 28 h to afford >99% conversion to 4-(lauramidomethylpyridinium-1-yl)acetate. $^1$H NMR (300 MHz, dmso-d$_6$) δ 8.73 (d, 2h, J=6.8 Hz); 8.68 (t, 1H, J=5.8 Hz); 7.81 (d, 2H, J=6.7 Hz); 4.84 (s, 2H); 4.50 (d, 2H, J=5.8 Hz); 2.21 (t, 2H, J=7.3 Hz), 1.6-1.4 (m, 2H); 1.22 (m, 20H), 0.85 (t, 3H, J=7.0 Hz).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 3.9 min.

Example 16

Preparation of 1-methyl-4-piperdinyl lauramide

To a 250-mL round bottom flask fitted with a Dean-Stark trap connected to a cold-finger condenser was added methyl laurate (45.0 g, 210 mmol), 4-amino-1-methylpiperidine (25.2 g, 220 mmol), and Novozym 435. Heptane (20 mL) was added to the mixture. The pressure was reduced to 60 mm Hg and controlled by a vacuum regulator. The mixture was heated to 65° C. After 2.5 hrs, solids began to form in the reaction mixture. The reaction was stopped. Ethyl acetate (200 mL) was added to the mix at 50° C. to dissolve the solids. The mixture was then filtered while hot through a frit. After the volatiles were removed at reduced pressure, the solids were triturated with heptane (200 mL) and stirred vigorously. The mixture was then filtered. The solids were placed in a 40° C. vacuum oven with nitrogen sweep overnight to afford the title compound as a white solid (21.0 g). $^1$H NMR (300 MHz, CDCl$_3$) δ 5.23 (m, 1H); 3.77 (m, 1H); 2.75 (m, 2H); 2.27 (s, 3H); 2.16-2.04 (m, 4H), 1.90 (m, 2H), 1.43 (m, 1H), 1.33-1.18 (m, 17H), 0.87 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 3.8 min.

Example 17

Preparation of (4-lauramido-1-methylpiperidinium-1-yl)acetate

To a 100-mL round bottom flask was added 1-methyl-4-piperdinyl lauramide (20.2 g, 64.9 mmol), sodium chloroacetate (8.70 g, 74.7 mmol), and sodium bicarbonate (1.09 g, 12.9 mmol). Ethanol (44.2 mL) was then added. The mixture was heated to 80° C. and stirred at this temperature for 14.25 hrs. HPLC analysis indicated 43% conversion. Water (2.21 mL) was then added to the mixture. At 16 hours, HPLC analysis indicated 69% conversion. At 20.75 hrs, HPLC indicated 99.2% conversion. After 2 hrs of additional reaction time, the mixture was cooled and concentrated to afford a sticky solid. Isopropanol (200 mL) was added to dissolve the solids. The mixture was heated to 65° C. and filtered while hot through 1-micron filter paper. The resulting solution was concentrated at reduced pressure. Isopropanol (200 mL) was added and the mixture was concentrated again. The solid was placed in a 45° C. vacuum oven with nitrogen sweep and dried overnight to afford (4-lauramido-1-methylpiperidinium-1-yl)acetate (13.14 g). $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.2, 4.4 min.

Surfactant Properties

The surfactant properties of the compounds of the formula 1 can be determined by a number of tests including an ASTM foam height test and a test for critical micelle concentration.

The Standard Test Method for Foaming Properties of Surface-Active Agents (ASTM 1173-07) was used to determine the foaming properties of the heterocyclic amphoteric compounds of the formula 1 described herein. This method generates foam under low-agitation conditions and is generally used for moderate- and high-foam surfactants. This test gathers data on initial foam height and foam decay. Foam decay provides information on foam stability.

The apparatus for carrying out this test includes a jacketed column and a pipet. The jacketed column serves as a receiver, while the pipet delivers the surface-active solution. Solutions of each surface-active agent were prepared. The solution of the heterocyclic amphoteric compound to be tested was added to the receiver (50 mL) and to the pipet (200 mL). The pipet was positioned above the receiver and opened. As the solution fell and made contact with the solution in the receiver, foam was generated. When the pipet was empty, the time was noted and an initial foam height was recorded. The foam height was recorded each minute for five minutes. Exact size specifications for the glassware can be found in ASTM 1173-07. The foam height results for each heterocyclic amphoteric compound 1 and representative standards are listed below in Tables 1 (0.1% concentration) and 2 (1% concentration).

The critical micelle concentration (CMC) was also determined for each compound. The CMC is the concentration of surfactant above which micelles spontaneously form. CMC is an important characteristic of a surfactant. At surfactant concentrations below the CMC, surface tension varies widely with surfactant concentration. At concentrations above the CMC, surface tension remains fairly constant. A lower CMC indicates less surfactant is needed to saturate interfaces and form micelles. Typical CMC values are less than 1 weight percent (10,000 ppm).

The fluorimetric determination of CMC described by Chattopadhyay and London (*Analytical Biochemistry*, Vol. 139, pp. 408-412 (1984)) was used to obtain the critical micelle concentrations found in Table 3 below. This method employs the fluorescent dye 1,6-diphenyl-1,3,5-hexatriene (DPH) in a solution of the surface-active agent. The analysis is based on differences in fluorescence upon incorporation of the dye into the interior of the micelles. As the solution exceeds CMC, a large increase in fluorescence intensity is observed. This method has been found to be sensitive and reliable, and has been demonstrated on zwitterionic, anionic, cationic, and uncharged surface-active agents.

TABLE 1

Foam height (cm) at time t (min) at 0.1 wt % concentration

| | Foam height (cm) at time t (min) 1 g/L (0.1 weight %) | | | | | |
|---|---|---|---|---|---|---|
| | t = 0 | 1 | 2 | 3 | 4 | 5 |
| Standard | | | | | | |
| cocamidopropyl betaine | 17.0 | 16.0 | 16.0 | 16.0 | ND | 15.5 |
| Compound from Example No. | | | | | | |
| 3 | 16.5 | 16.0 | 15.5 | 15.5 | 15.5 | 15.5 |
| 5 | 16.5 | 16.0 | 15.5 | 15.5 | 15.0 | 15.0 |
| 7 | 16.0 | 14.5 | 12.5 | 9.0 | 6.0 | 4.0 |
| 9 | 17.0 | 17.0 | 16.5 | 16.5 | 16.0 | 16.0 |
| 11 | 18.5 | 17.5 | 17.5 | 17.0 | 16.5 | 16.0 |

ND = not determined

TABLE 2

Foam height (cm) at time t (min) at 1.0 wt % concentration

| | Foam height (cm) at time t (min) 10 g/L (1.0 weight %) | | | | | |
|---|---|---|---|---|---|---|
| | t = 0 | 1 | 2 | 3 | 4 | 5 |
| Standard | | | | | | |
| cocamidopropyl betaine | 17.5 | 16.5 | ND | 16.0 | 16.0 | 16.0 |
| Compound from Example No. | | | | | | |
| 3 | 18.5 | 18.0 | 17.5 | 17.0 | 17.0 | 17.0 |
| 5 | 18.0 | 17.5 | 17.0 | 17.0 | 17.0 | 16.5 |
| 7 | 18.0 | 17.0 | 17.0 | 17.0 | 16.5 | 16.5 |
| 9 | 16.5 | 16.0 | 16.0 | 15.5 | 15.5 | 15.5 |
| 11 | 19.0 | 18.0 | 18.0 | 17.5 | 17.5 | 17.5 |

ND = not determined

As the data in Tables 1 and 2 indicate, solutions of the amphoteric heterocyclic compounds 1 generated large amounts of foam. Examples in which the foam height did not significantly decrease over time indicate good foam stability.

TABLE 3

Critical micelle concentrations

| | CMC (ppm) | CMC (mM) |
|---|---|---|
| Standards | | |
| sodium lauryl sulfate | 2386 | 8.27 |
| ammonium lauryl sulfate | 392 | 1.38 |
| cocamidopropyl betaine | 24.5 | 0.069 |
| Compound from Example No. | | |
| 3 | 22.9 | 0.062 |
| 5 | 23.7 | 0.062 |
| 7 | 19.2 | 0.050 |
| 11 | 95.0 | 0.248 |
| 17 | 566.5 | 1.54 |

The data in Table 3 indicate that very low concentrations of the heterocyclic amphoteric compounds 1 are needed to reach the critical micelle concentration. These values fall in the range of useful surface-active agents, and compare well with standard surfactants.

Stability Properties

It was unexpectedly found that the heterocyclic amphoteric compounds of the invention can be more stable at lower pH conditions than the corresponding amphoteric ester betaines disclosed in US 2012/0277324 A1. For example, as seen in Table 4 below, there was limited loss of the heterocyclic amphoteric compound under extended incubation in pH 4.5 water at 50° C. (Example 18), while there was significant loss of the similar, but non-heterocyclic ester betaine, even under milder conditions (Comparative Example 2).

Comparative Example 1

Preparation of 3-(cocoyloxypropyldimethylammonio)acetate

To a 3-L reactor equipped with a condenser and an overhead stirrer was added 3-dimethylaminopropyl cocoate (350.42 g; 1.21 mol), sodium chloroacetate (155 g, 1.33 mol, 1.1 eq), sodium bicarbonate (20.32 g; 0.24 mol; 0.2 equiv) and water (807 g). The reaction mixture was stirred and heated to an internal temperature of 76° C. for 12 hours to afford >98% conversion according to HPLC analysis. The mixture was cooled to ambient temperature, and the pH was adjusted to 6.5 by the addition of 3 M HCl. The resulting mixture was clarified to afford 1267 g of a clear yellow liquid. Analysis of the mixture by HPLC indicated a 29.6 wt % solution of 3-(cocoyloxypropyldimethylammonio)acetate in water. $^1$H NMR analysis was consistent with the product structure.

HPLC (150×4.6 mm Zorbax SB-C8 column, 80:20 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 3.5 min.

Example 18

Stability study of (4-lauroyloxy-1-methylpiperidinium-1-yl)acetate

The material prepared in Example 9 (20 mL) was combined with 210 mg of citric acid hydrate, and the pH was lowered to 4.5 by the addition of aqueous HCl. The resulting mixture was placed in a 50° C. oven. Samples were taken periodically and analyzed for the amount of (4-lauroyloxy-1-methylpiperidinium-1-yl)acetate remaining by quantitative HPLC. The results are in Table 4 below.

Comparative Example 2

Stability study of 3-(cocoyloxypropyldimethylammonio)acetate

The material prepared in Comparative Example 1 was adjusted to pH 5 by the addition of aqueous HCl and then placed in a 45° C. oven. Samples were taken periodically and analyzed for the amount of 3-(cocoyloxypropyldimethylammonio)acetate remaining by quantitative HPLC. The results are in Table 4 below.

TABLE 4

Stability of Heterocyclic versus Non-Heterocyclic Ester Carboxy Amphoterics

| | Percent amphoteric remaining | |
|---|---|---|
| | Example 18 (heterocyclic) | Comparative Example 2 (non-heterocyclic) |
| Conditions | pH 4.5, 50° C. | pH 5, 45° C. |
| Time (weeks) | | |
| 0 | 100% | 100% |
| 2 | 98% | 74% |
| 6 | 96% | ND |
| 8 | 85% | 73% |

ND = not determined

The invention has been described in detail with particular reference to preferred embodiments thereof, but it will be understood that variations and modifications can be effected within the spirit and scope of the invention.

We claim:

1. A compound having the formula 1:

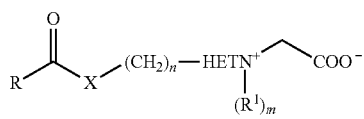

wherein
R is a $C_3$-$C_{23}$ hydrocarbyl group;
$R^1$ is a $C_1$-$C_8$ hydrocarbyl group selected from $C_1$-$C_6$ alkyl or alkenyl and $C_3$-$C_8$ cycloalkyl;
HETN is a piperidine group;
X is O or NH;
n is 0 or 1; and
m is 1.

2. The compound according to claim 1, wherein the hydrocarbyl group of R is optionally substituted with one to five substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

3. The compound according to claim 2, wherein the hydrocarbyl group of R is mono-unsaturated or poly-unsaturated.

4. The compound according to claim 1, wherein R is a $C_3$-$C_8$ cycloalkyl group optionally substituted with one to five substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

5. The compound according to claim 1, wherein the hydrocarbyl group of $R^1$ is optionally substituted with one to three substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, heteroaryl, thioether, $C_2$-$C_{10}$ dialkylamino, $C_3$-$C_{15}$ trialkylammonium, chlorine, and bromine.

6. The compound according to claim 1, wherein the hydrocarbyl group of $R^1$ is $C_1$-$C_6$ alkyl or alkenyl.

7. The compound according to claim 1, wherein $R^1$ is a $C_3$-$C_8$ cycloalkyl group optionally substituted with one to three substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

8. The compound according to claim 1, wherein
R is selected from the group consisting of $C_5$-$C_{19}$ alkyl, $C_5$-$C_{17}$ alkenyl, $C_5$-$C_{17}$ dienyl, and $C_3$-$C_8$ cycloalkyl;
$R^1$ is a $C_1$-$C_6$ alkyl group; and
HETN is a piperidine group.

9. The compound according to claim 1, wherein
RCO— is octanoyl, decanoyl, lauroyl, myristoyl, or a $C_6$ to $C_{20}$ acyl radical derived from coconut oil, hydrogenated coconut oil, or hydrogenated and/or fractionated coconut oil fatty acids;
$R^1$ is methyl;
HETN is a 3-piperidine group or a 4-piperidine group; and
m is 1.

10. The compound according to claim 9, wherein RCO— is lauroyl.

11. The compound according to claim 1, wherein the compound is selected from the group consisting of (4-cocoyloxy-1-methylpiperidinium-1-yl)acetate, (3-cocoyloxymethyl-1-methylpiperidinium-1-yl)acetate, (4-cocoyloxymethyl-1-methylpiperidinium-1yl)acetate, (4-lauroyloxy-1-methylpiperidinium-1-yl)acetate, (3-lauroyloxymethyl-1-methylpiperidinium-1-yl)acetate, and (4-lauramido-1-methylpiperidinium-1-yl)acetate.

12. A process for preparing a compound having the formula 1:

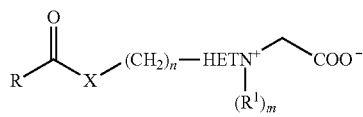

wherein
R is a $C_3$-$C_{23}$ hydrocarbyl group;
$R^1$ is a $C_1$-$C_8$ hydrocarbyl group;
HETN is a piperidine group;
X is O or NH;
n is 0 or 1; and
m is 1,
the process comprising:
(a) contacting an acid or ester of formula 2 with a heterocyclic alcohol of formula 3 or a heterocyclic amine of formula 4:

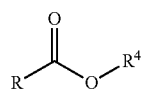

in the presence of an enzyme at conditions effective to form an intermediate of formula 5:

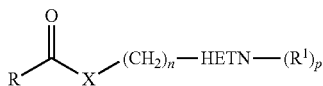

wherein
R, $R^1$, X, HETN, and n are as defined above,
$R^4$ is hydrogen or a $C_1$-$C_6$ alkyl group, and
p is 1; and
(b) contacting the intermediate of formula 5 with an acetic acid alkylating agent at conditions effective to form the compound of formula 1.

13. The process according to claim 12, wherein the enzyme is a lipase.

14. The process according to claim 13, wherein the lipase is from *Pseudomonas* sp or *Candida antarctica*.

15. The process according to claim 13, wherein the lipase is immobilized on a support selected from the group consisting of ceramic, diatomaceous earth, acrylic resin, and a porous fluoropolymer.

16. The process according to claim 12, wherein step (a) is carried out at a temperature of 50 to 90° C. and a pressure of 10 Torr (1,333 Pa) to ambient pressure.

17. The process according to claim 12, wherein step (a) is carried out in the presence of an aromatic or aliphatic hydrocarbon solvent.

18. The process according to claim 12, wherein step (a) is carried out in the absence of an added solvent.

19. The process according to claim 12, which further comprises removing water or alcohol by-product from the reaction mixture during step (a).

20. The process according to claim 12, wherein step (b) is carried out at a temperature of 50 to 125° C.

21. The process according to claim 12, wherein step (b) is carried out in the presence of a base selected from the group consisting of metal hydroxides, metal carbonates, and metal bicarbonates.

22. The process according to claim 12, wherein step (b) is carried out in the presence of a solvent.

23. The process according to claim 22, wherein the solvent is selected from the group consisting of water, $C_2$-$C_5$ alcohols, ether-alcohols, and mixtures thereof.

24. The process according to claim 12, wherein the acetic acid alkylating agent is sodium chloroacetate or chloroacetic acid neutralized in situ with sodium hydroxide.

25. The process according to claim 12, wherein
R is selected from the group consisting of $C_5$-$C_{19}$ alkyl, $C_5$-$C_{17}$ alkenyl, $C_5$-$C_{17}$ dienyl, and $C_3$-$C_8$ cycloalkyl;
$R^1$ is a $C_1$-$C_6$ alkyl group; and
HETN is a piperidine group.

26. The process according to claim 12, wherein
RCO— is octanoyl, decanoyl, lauroyl, myristoyl, or a $C_6$ to $C_{20}$ acyl radical derived from coconut oil, hydrogenated coconut oil, or hydrogenated and/or fractionated coconut oil fatty acids;
$R^1$ is methyl;
HETN is a 3-piperidine group or a 4-piperidine group; and
m is 1.

27. The process according to claim 26, wherein RCO— is lauroyl.

28. The process according to claim 12, wherein the compound of the formula 1 is selected from the group consisting of (4-cocoyloxy-1-methylpiperidinium-1-yl)acetate, (3-cocoyloxymethyl-1-methylpiperidinium-1-yl)acetate, (4-cocoyloxymethyl-1-methylpiperidinium-1yl)acetate, (4-lauroyloxy-1-methylpiperidinium-1-yl)acetate, (3-lauroyloxymethyl-1-methylpiperidinium-1-yl)acetate, and (4-lauramido-1-methylpiperidinium-1-yl)acetate.

* * * * *